US005646727A

United States Patent [19]

Hammer et al.

[11] Patent Number: 5,646,727
[45] Date of Patent: Jul. 8, 1997

[54] PERISTALTIC PUMP

[75] Inventors: Michael Ron Hammer, Sassafras; Christopher John Park, Mulgrave; Brian Lawrence Allen, Berwick; Thomas Robert Turney, Olinda, all of Australia

[73] Assignee: Varian Associates, Inc., Palo Alto, Calif.

[21] Appl. No.: 378,028

[22] Filed: Jan. 24, 1995

[51] Int. Cl.[6] .......... G01J 3/30

[52] U.S. Cl. .......... 356/315

[58] Field of Search .......... 356/315, 316, 356/312

[56] References Cited

U.S. PATENT DOCUMENTS 4,228,930 10/1980 Hogan .
4,989,976 2/1991 Huber .......... 356/315

FOREIGN PATENT DOCUMENTS

0013002A1 7/1980 European Pat. Off. .
130374A2 1/1985 European Pat. Off. .
120284A1 10/1985 European Pat. Off. .
0164020A1 12/1985 European Pat. Off. .
2069063 8/1981 United Kingdom .
2082261 3/1982 United Kingdom .
2226601 7/1990 United Kingdom .
WO81/01656 6/1981 WIPO .

*Primary Examiner*—K. Hantis
*Attorney, Agent, or Firm*—Edward H. Berkowitz

[57] ABSTRACT

A peristaltic pump comprises a rotatable drum 2 having rollers 5 or cams 5' for squashing a flexible tube 9 against a profiled surface 10 of a presser plate 7. Tube 9 is mounted between supports 14 and 15 on presser plate 7 and is automatically movable between an inoperative and operative (pumping) position by pivotal movement of plate 7 about axis 8 produced by an electro mechanical actuator. A flexible membrane 33 is sandwiched between rollers 5 or cams 5' for eliminating shear forces on the tube 9. The construction of the pump and shape of profile 10 are such as to mimimise pulsations in the output flow. Systems for supplying a sample for analysis to spectroscopic apparatus using the peristaltic pump are also described.

5 Claims, 5 Drawing Sheets

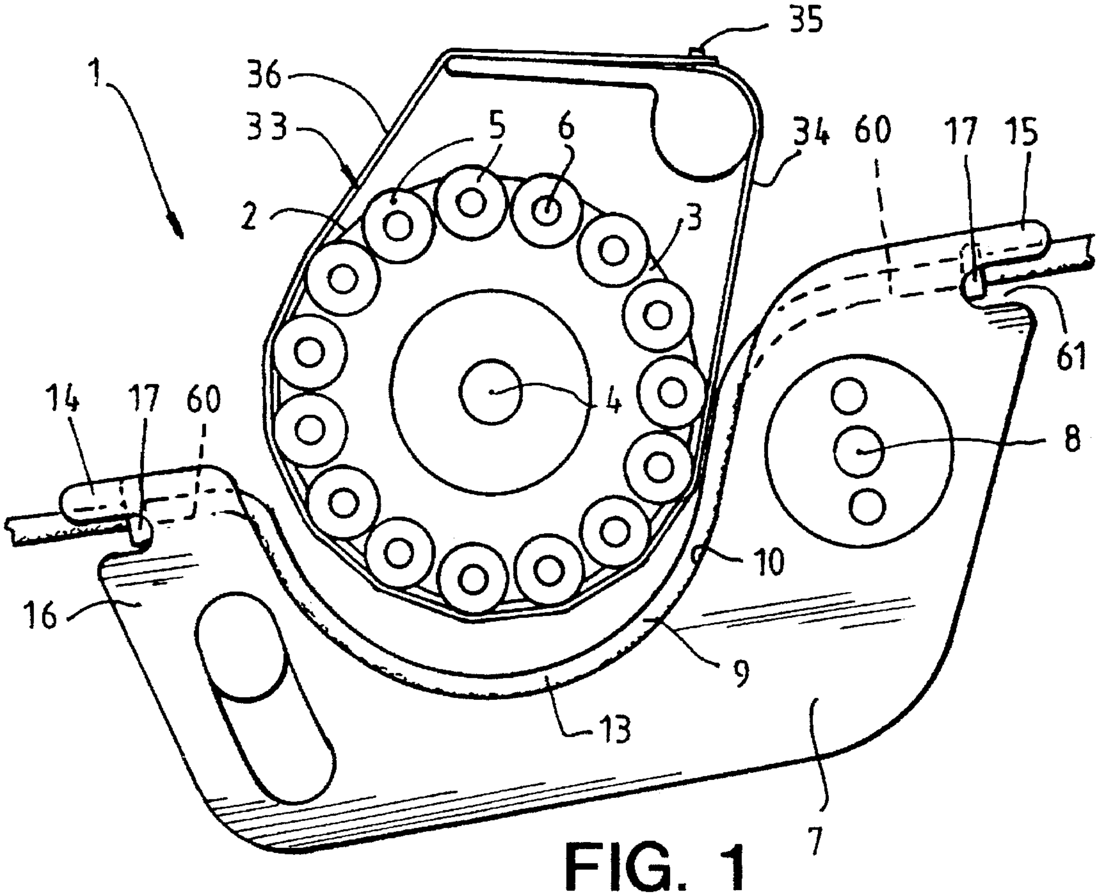
FIG. 1
FIG. 2
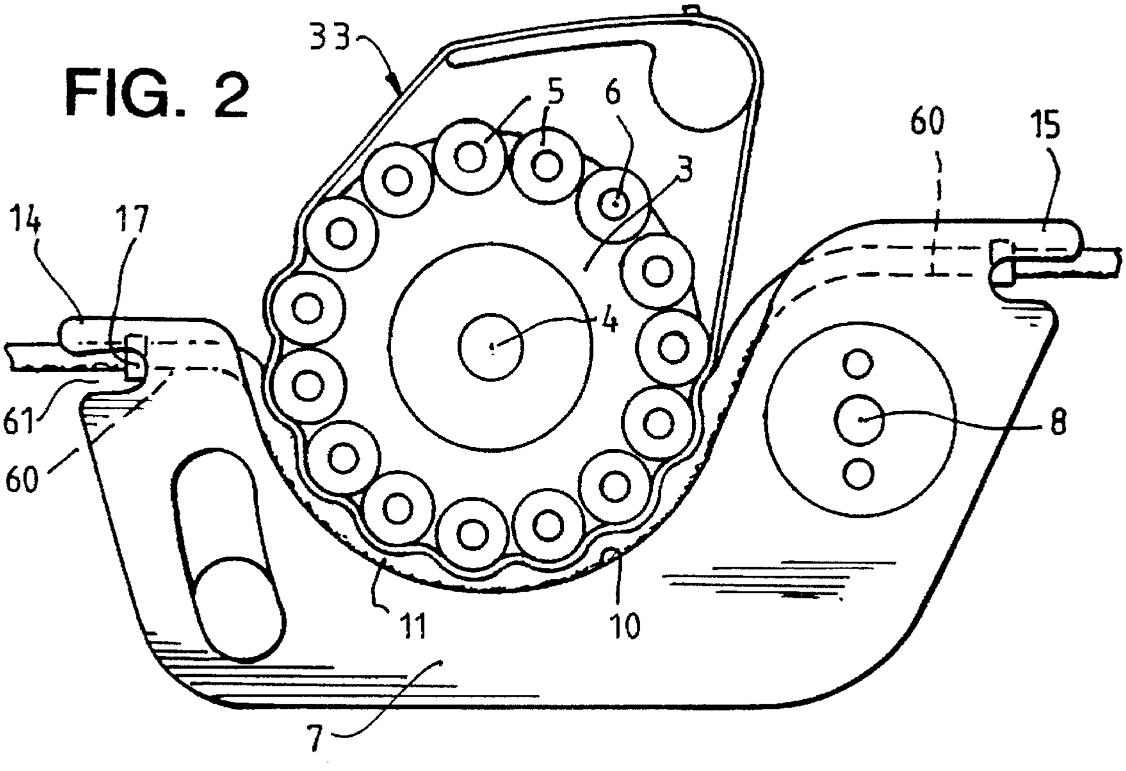

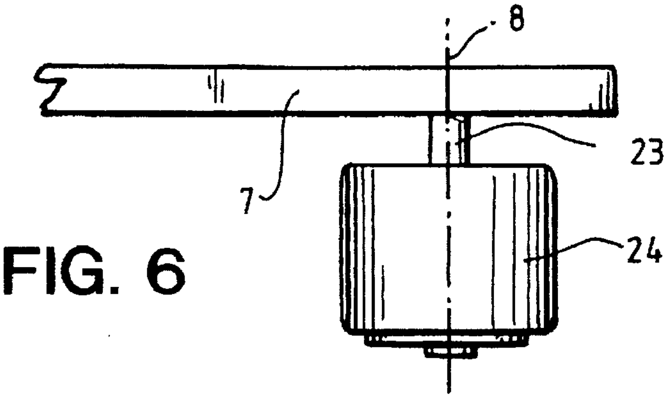
FIG. 6
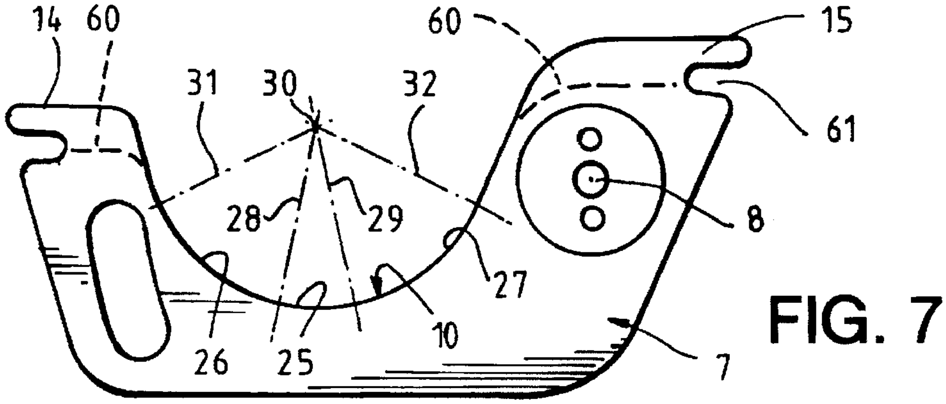
FIG. 7
FIG. 8
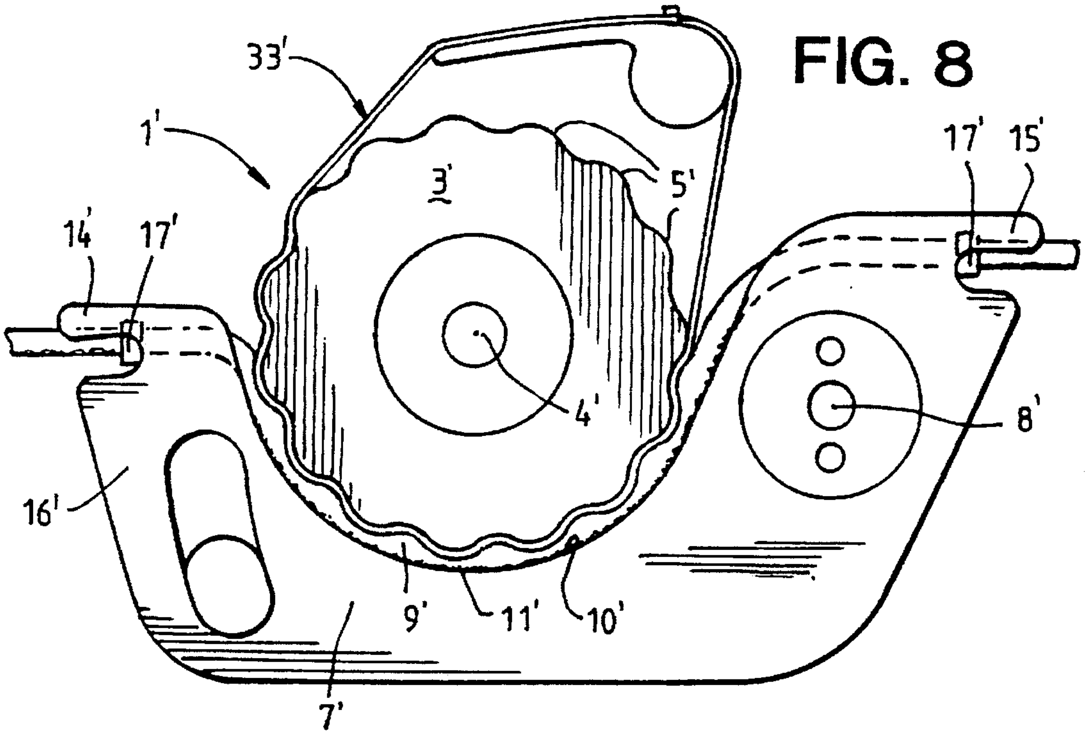

PERISTALTIC PUMP

TECHNICAL FIELD

This invention relates to peristaltic pumps and particularly but not exclusively such pumps intended for use in circumstances where the amount of material pumped over a given time period needs to be accurately controlled. One such circumstance is the presentation to spectroscopic apparatus of a sample to be analysed by that apparatus. This invention also relates to spectroscopic analysis of substances and is particularly concerned with a system and method whereby samples are presented for analysis by spectroscopic apparatus. It will be convenient to hereinafter describe in the invention relation to spectroscopic apparatus, but it is to be understood that a pump according to the invention has other applications.

BACKGROUND

Peristaltic pumps are well known and comprise a rotatable drum having a plurality of rollers located around its periphery, and a flexible tube which is held against the drum periphery by a presser plate and through which liquid (for example) is pumped. The tube is held by two spaced fixed supports, and liquid is caused to move through the tube in response to a moving pinch zone caused by the rollers pressing on the tube as the drum rotates.

Pumps of the foregoing kind suffer problems which tend to make them unsuitable for use in certain circumstances. One such problem is a tendency for the tube to become distorted and to take on a permanent set which makes it unsuitable for further work. In operation, the tube is pulled over the drum and is attached to the fixed supports so as to have a correct amount of longitudinal tension. If the tube is left in the operating position for extended periods of time with the pump stationary, the aforementioned distortion may occur. Consequently, it is good practice to release the presser plate and the tube tension at the end of each period of use, but that is often overlooked either by accident or by design, particularly as the re-establishment of the pump to an operative condition is a tedious process.

Another problem with peristaltic pumps is that the output flow is a pulsating flow, and that tends to make such pumps unsuitable for use in some circumstances. For example, the pulsating flow makes such pumps unsuitable for use in delivering a sample to be analysed to the nebulizer of a spectroscopic instrument. That difficulty can be met by operating the pump at a very high speed but such operation is not always possible or convenient.

Another problem in peristaltic pumps that are to be used for accurately metering materials and which is a significant component in their cost, is that dimensional tolerances in the manufacture of individual components, such as the drum and the rollers, and positional tolerances on assembling the different parts are necessarily quite small to ensure the requisite accuracy in operation of the pump. Also the roller bearings in known pumps often corrode and produce unreliable operation.

DISCLOSURE OF THE INVENTION

It is an object of the present invention to provide a peristaltic pump in which one or more of the aforementioned problems are ameliorated. It is another object of an embodiment of the invention to provide a peristaltic pump of relatively simple construction and which is relatively inexpensive to manufacture.

A peristaltic pump according to the broadest aspect of the invention is characterised in that at least one of the tube supports is movable relative to the drum between loaded and unloaded positions rather than having a fixed position relative to the drum as in prior constructions.

Thus, according to this broadest aspect of the invention, there is provided a peristaltic pump including a rotatable drum including compressing elements around its periphery, a flexible tube extending between two spaced supports and a movable presser plate for holding the tube against the periphery of the drum between the two spaced supports such that on rotation of the drum the compressing elements squeeze the tube against the presser plate for moving fluid through the tube, wherein at least one of the tube supports is movable relative to the drum to establish an operative and an inoperative position for the tube, the operative position being when the tube is positioned for pumping.

Preferably, the movable support is fixed to or formed integral with the presser plate so as to move with that plate between the loaded and unloaded positions.

It has been conventional practice in the past to secure the presser plate in the pump operative position by means of a spring influenced clamp or the like. According to a preferred form of the present invention, the presser plate is moved into the operative position by means of an electro-mechanical actuator. It is further preferred that the arrangement is such that the presser plate is subjected to a control system such that it can be moved automatically between operative and inoperative positions thereof. Thus, in this preferred arrangement, a peristaltic pump is provided in which the tube tension is automatically established as the pump is being conditioned for operation and is automatically de-established at the end of each operating sequence.

A further aspect of the invention is that the known rotatable drum and rollers assembly in a peristaltic pump according to the invention may be replaced by a cam, the profile of which comprises a plurality of camming surfaces for squeezing the tube. Thus a pump according to the invention will contain tube compressing elements which may be in the form of rollers or fixed camming surfaces around the periphery of the drum.

A further feature in a pump according to the invention is that the presser plate may be profiled in such a way as to minimise pulsations and lack of stability in the output flow. That profiling is applied to the surface of the presser plate which is opposed to the drum and is therefore the surface which holds the tube against the drum rollers or camming surfaces. Preferably the profiled presser plate surface includes or is composed of at least two regions, a pinch region and an expansion region which is located downstream of the pinch region in relation to the direction of flow through the tube. The pinch region is arranged to cooperate with the drum rollers or camming surfaces so that the aforementioned pinch zones are created within that region. The expansion region preferably follows immediately after the pinch region and is arranged so that the space between it and the drum progressively increases in the downstream direction. In one arrangement, there is a third region upstream of the pinch region, which is called an entrance region and which is arranged so that the space between it and the drum progressively decreases in the downstream direction.

The operation of a peristaltic pump is essentially equivalent to moving a restriction along the length of the tube so that liquid within the tube and in advance of the restriction is pushed through the tube by the restriction. There is in fact a plurality of such restrictions which are created in sequence by the rollers or camming surfaces as they are moved against that section of the tube which is influenced by the presser plate. As each roller or cam moves away from that section of the tube, it allows the tube to expand and thereby increase the internal volume of the tube downstream of the presser plate. That expansion gives rise to pulsations in the output flow of the pump.

Adoption of a presser plate having an expansion region as described above enables output flow pulsations to be eliminated, or at least reduced. This is achieved by designing the profile of the expansion region so that a substantially linear relationship exists between the angular rotation of the drum and the increase in the tube internal volume resulting from withdrawal of a drum roller or cam from the tube. Ideally the linear relationship should be such as to increase the internal volume by the volume contained by a single tube pinch over an angular rotation equivalent to the angular separation of one roller or camming surface from the next, and then the output flow is free of pulsations. In other circumstances, a strictly linear relationship may not be possible, but it is nevertheless possible to reduce the amplitude of the pulsations to an acceptable level by means of profiling as discussed above.

The presser plate may furthermore be profiled such that over a portion of said profile, the gap between the camming surfaces, or rollers of the rotating drum, and said portion is less than that which is necessary to seal the tube. In operation, the camming surfaces or rollers "over-squash" the tube, thus allowing for a lesser degree of accuracy in sizing and assembling the pump parts in manufacture, although the primary aim of this feature is to allow a lesser degree of relative positioning accuracy of the pump parts.

Another cause of pulsation in the output flow in pump constructions wherein the compressing elements are tellers is frictional resistance to rotation of the rollers. Each roller rotates in response to a tangential force created between it and the pump tube, which is held against movement with the drum. That force tends to stretch the tube longitudinally and also generates shear forces in the tube because the side of the tube contacting the presser plate does not experience the same tangential forces. Such shear forces contribute to tube wear and fatigue failure. Also, as each roller withdraws from the tube, the tube is able to relax longitudinally and thereby cause a change in the internal volume of the tube such as to introduce pulsations into the output flow.

Prior attempts to meet the problem have not been entirely satisfactory. One approach has been to reduce frictional resistance to roller rotation by mounting the rollers on ball bearings, but that is a complex and costly approach which alleviates the problem rather than solves it. Another approach has been to drive the rollers through a planetary gear system, and that is a very expensive approach which also fails to solve the problem. In order to be effective, the rotational speed of the rollers must exactly match the traverse speed of the drum over the tube, but such matching is seldom achieved.

According to a further preferred feature of the invention, the aforementioned problem is met or at least substantially alleviated by interposing a flexible membrane between the drum and the tube such that the membrane rather than the tube absorbs the aforementioned shear forces. The membrane is anchored upstream of the region within which the tube is pinched as previously described, and is preferably composed of a material which is not prone to stretch in the longitudinal direction of the tube. Suitable materials include polyester such as Mylar and other plastics materials, and metal foil, but that is not an exhaustive list.

In a pump having camming surfaces instead of rollers, the frictional forces on the tube will be larger. Thus in this form of pump construction a flexible membrane needs to be interposed between the cam and the tube for absorbing shear forces that would otherwise act on the tube. It is desirable for the contacting surfaces of the cam and the membrane to be lubricated and such lubrication may be provided by a lubricating substance, for example a silicone grease, placed on the membrane or camming surfaces. Alternatively the membrane or camming surfaces may be self lubricating. Preferably the membrane is of a substance or constructed such that its cam facing surface is very slippery, for example the membrane may be a laminate of Mylar and a more slippery plastic.

When a flexible membrane is disposed between the drum and the tube as described above, the tension applied to the tube when it is in its operative position is preferably very little (that is, it is close to zero or even zero) so that the elasticity of the tube defines a volume of liquid between adjacent rollers or cams which is independent of roller (or cam) speed. Thus, the tube is preferably held reasonably loosely in its operative position and there is minimal or zero stretching of the tube.

Where the presser arm force is generated by an electromechanical actuator such as a stalled DC motor run at a controlled current, friction or other effects in the actuator may cause uncertainty in the output torque and hence presser plate force. This uncertainty is undesirable and may be overcome by cycling the current setpoint about its mean value at a rate fast enough to not affect operation of the system, yet slow enough for the actuator to respond.

One technique employed in spectroscopy is to produce a sample solution containing the substance of interest, and to introduce that solution into a nebulizer which directs an atomized body of the solution into a flame or plasma. Preparation of such samples is an exacting and time consuming operation, and obtaining a suitable level of dilution is one particular problem in that preparation. In addition to the sample solutions, it is necessary to prepare standard solutions for comparative reference, and that adds further to the time required to conduct the sample analysis.

There have been several proposals for overcoming or alleviating all or some of the foregoing problems. One such proposal is that of Jones as described in "Atomic Absorption Newsletter", Vol. 9, No. 1, January-February 1970, pages 1 to 5. The Jones proposal involves connecting separate sample solution and diluent supplies to the nebulizer through a T junction, and delivering the sample to that junction by way of a variable speed syringe pump. Fluid flows into the nebulizer at the natural aspiration rate of the system. The flow rate of the sample is controlled by the pump speed, and the flow of diluent automatically adjusts so that the total flow rate is constant. Suitable variation of the pump speed then results in achievement of a desired level of dilution in the sample stream presented to the nebulizer.

A deficiency of the Jones proposal is that it utilizes the same pump for standard and sample solutions respectively. In particular, it is necessary to replace the supply of one solution with the supply source of the other when it is required to switch from analysis of one solution to the other. It also uses a syringe pump and this involves carryover, slow throughput, limited volume and wasted sample problems.

The use of a peristaltic pump according to the present invention in a system for delivering a sample for analysis to spectroscopic apparatus offers the advantage that a more even flow of sample into the apparatus is achievable than is the case with prior such systems.

Thus an object of a further aspect of the present invention is to provide an improved method and apparatus for preparing and introducing solutions for analysis.

Accordingly the invention also provides a system for delivering a sample for analysis to spectroscopic apparatus, including means for supplying a stream of sample solution, means for supplying a stream of diluent, means for combining the two streams, and means for delivering the combined stream into a nebulizer of the spectroscopic apparatus at a substantially constant flow rate, wherein the means for supplying a stream of sample solution or the means for supplying a stream of diluent includes a peristaltic pump according to the invention, and the system is arranged such that on variation of the flow rate of the stream of sample solution or the stream of diluent, the other stream (of diluent or sample solution) is automatically varied to maintain said substantially constant flow rate into said nebulizer.

The invention also provides a method of spectroscopic analysis, wherein a system as just described is used to supply a sample to a nebulizer of spectroscopic apparatus for calibration of that apparatus and for analysis of the sample, the method including supplying streams of sample solution from a single on-line source of the sample solution, In a method and apparatus according to the further aspect of the invention, separate streams of sample solution and diluent respectively are combined and then introduced into the nebulizer as a single stream. The flow rate of the combined stream into the nebulizer is fixed by the natural aspiration rate of the nebulizer, and the cross-sectional size of the passage through which the combined stream enters the nebulizer. The sample solution and the diluent are fed separately to a junction (that is a mixing point) at which the combined stream is formed, and either the sample solution or the diluent is delivered to that junction by a variable speed peristaltic pump according to the invention. Preferably, the pump delivers the sample solution to the junction, and diluent is induced into the stream leaving the junction by a pressure differential existing between the nebulizer and the junction. As the flow via the peristaltic pump changes, the flow of the diluent stream automatically changes to compensate. This changing flow results in a changed pressure drop between the diluent reservoir and mixing point. Such a pressure change could alter the pressure differential at which the nebuliser operates and thus alter its uptake rate, affecting overall system performance. To avoid this happening, it is desirable to ensure pressure changes at the mixing point are small relative to the pressure drop between the mixing point and the nebuliser. This can be achieved by ensuring the tubing bore between the mixing point and reservoir is substantially larger than between the mixing point and nebuliser. To achieve 1% accuracy, a ratio of bore diameter of at least 3:1 is desirable, with higher ratio's preferable.

Assuming the maximum flow from the junction to the nebulizer is fixed at F1, and the flow rate of sample solution to the junction is F2, which is less than F1, diluent will be induced to flow into the junction at a rate equivalent to F1 minus F2. Variation of F2 by appropriate adjustment of the pump then automatically results in a variation in the diluent flow rate, and consequently the dilution ratio of the stream entering the nebulizer.

In a preferred form of the system and method, standard solution is able to be introduced into the aforementioned Junction under the influence of a second peristaltic pump according to the invention. Such an arrangement enables standard additions to be carried out in a simple and effective manner as hereinafter described.

DESCRIPTION OF DRAWINGS

It will be convenient to hereinafter describe the invention in further detail by reference to example embodiments which are shown in the attached drawings. The particularity of those drawings and the associated description is not to be understood as superseding the generality of the preceding broad description of the invention according to each of its aspects.

FIG. 1 is a diagrammatic view of a peristaltic pump according to one embodiment of the invention in which the presser plate is in the pump inoperative position.

FIG. 2 is a view similar to FIG. 1 but showing the presser plate in the pump operative position.

FIG. 6 is a side elevation view of yet another drive arrangement for the presser plate.

FIG. 7 is an enlarged view of one form of presser plate suitable for use in the pump of FIGS. 1 and 2.

FIG. 8 is a view similar to FIG. 2, but in which the peristaltic pump includes camming surfaces in place of rollers.

DETAILED DESCRIPTION OF EMBODIMENTS

Figure 3:
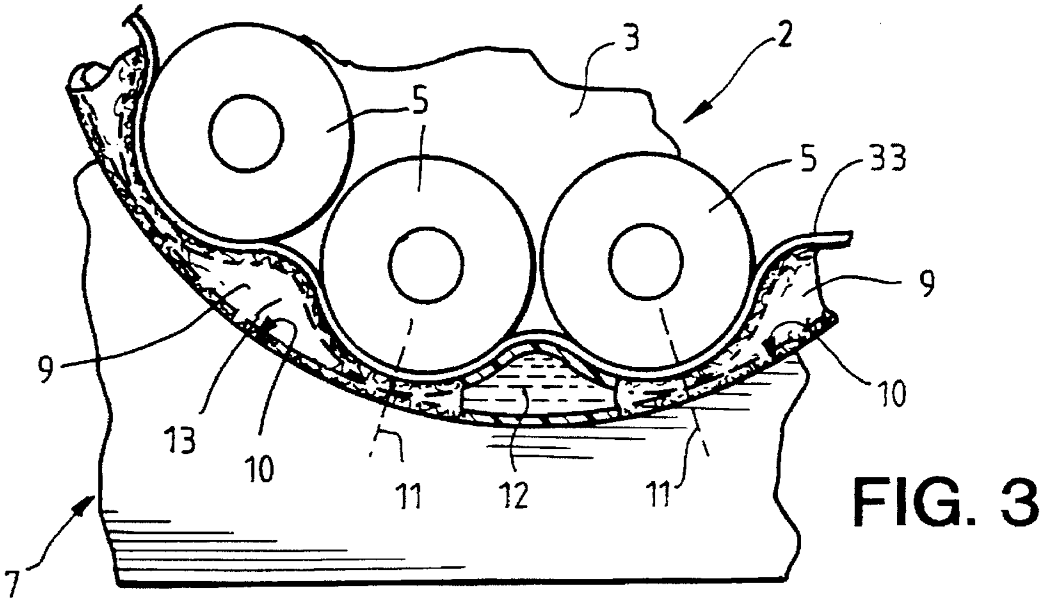
FIG. 3 is an enlarged view of part of the assembly shown in FIG. 2.

The example pump 1 shown in FIG. 1 includes a rotatable drum 2 having a body 3 arranged for rotation shout an axis 4, and a plurality of rollers 5 attached to the drum body 3 so as to extend as a continuous series around the periphery of that body 3. Each roller 5 is arranged to rotate relative to the drum body 3 about its own individual axis 6. Any suitable drive means may be provided to cause rotation of the drum 2.

A presser plate 7 is mounted on a support (not shown) so as to be rotatable about an axis 8 to adopt either a pump inoperative position or a pump operative position, which are shown in FIGS. 1 and 2 respectively. A flexible tube 9 is interposed between an operative surface 10 of the presser plate 7 and the periphery of the drum 2. When the presser plate 7 is in the operative position as shown in FIG. 2, a portion of the tube 9 which is trapped between the surface 10 and the rollers 5 is distorted as shown in FIG. 3. A pinch zone 11 is thereby created between each roller 5 and the plate surface 10 so that a body of liquid 12 within the tube 9 is trapped between each two adjacent zones 11. As the drum 2 rotates relative to the tube 9 the zones 11 move along the length of the tube 9 and thereby move the liquid bodies 12 in the same direction.

The tube 9 may be held against movement with the drum 2 in any suitable fashion. It is a characteristic of the particular construction shown however, that a section 13 of the tube 9 is held at two supports 14 and 15, and that the support 14 is attached to or formed integral with a portion 16 of the presser plate 7 which is located remote from the plate axis 8. The arrangement is such that movement of the plate 7 about the axis 8 causes the plate portion 16 to move towards or away from the periphery of the drum 2, and the tube support 14 is moved accordingly. In the particular arrangement shown, the other tube support 15 is also attached to or formed integral with the presser plate 7, but at a location adjacent the axis 8 so that there is relatively little movement towards and away from the drum 2.

Any suitable means may be utilised to hold the tube 9 at each of the supports 14 and 15. By way of example, two saddles 17 may be secured (for example by an adhesive) to the tube 9 against relative movement and arranged in spaced relationship such that each is cooperable with a respective one of the supports 14 and 15. Each support 14,15 is formed by a channel 60 in an end face of presser plate 7 and an intersecting groove 61 (see FIG. 7).

Figure 4:
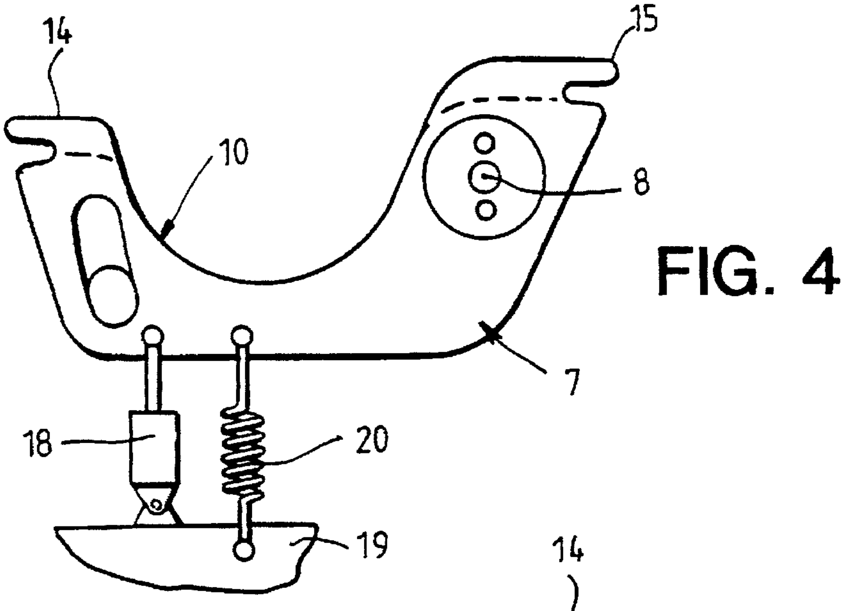
FIG. 4 is a diagrammatic view of one arrangement for driving the presser plate of the pump shown in FIGS. 1 and 2.

Movement of the presser plate 7 about the axis 8 can be achieved through use of any suitable drive means. It is preferred however, that an electro-mechanical actuator is used for that purpose. By way of example, the actuator may include a solenoid 18 as Shown in FIG. 4 which is connected between the presser plate 7 and a support 19. In the particular arrangement shown in FIG. 4, the solenoid 18 operates when energised to move the plate 7 to the pump operative position of FIG. 2, and a spring 20 functions to move the plate 7 to the pump inoperative position when the solenoid 18 is de-energised. In an alternative arrangement which is not shown, a spring could move the plate 7 to the operative position and a solenoid could operate to move the plate 7 to the inoperative position.

Figure 5:
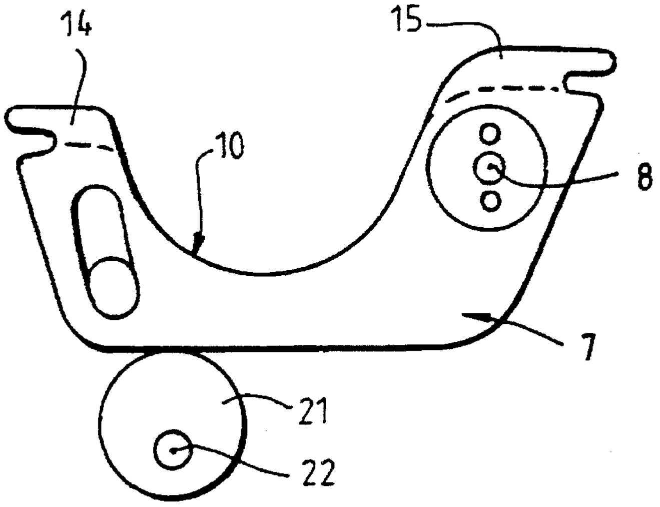
FIG. 5 is a view similar to FIG. 4 but showing an alternative drive arrangement.

FIG. 5 shows another possible drive arrangement for the plate 7 in which a cam 21 is caused to rotate about an axis 22 by means of a suitable drive motor (not shown). The arrangement is such that the rotational position of the cam 21 determines the position of the plate 7 relative to the drum 2. Any suitable means, such as a spring (not shown), may be used to hold the plate 7 in contact with the cam 21.

A preferred drive arrangement for the plate 7 is shown diagrammatically in FIG. 6. According to that arrangement, the plate 7 is mounted directly on to the shaft 23 of a drive motor 24, which could be a gear motor or a rotatable solenoid, for example. The bearings which support the shaft 23 determine the pivot axis 8 of the plate 7, and the plate 7 is connected to the shaft 23 so that rotation of the shaft 23 causes movement of the plate 7 between the pump operative and inoperative positions. Such an arrangement is extremely simple and involves a minimum number of mechanical parts. The arrangement may be such that the drive motor 24 stalls at the pump operative position, and consequently has the characteristic of a current to torque converter when driven at a controlled current. Thus, the torque and consequently the force applied by the plate 7 to the tube 9, can be controlled by variation of the current applied to the motor 24. Any suitable means may be adopted to guard against overload of the motor 24.

It will be appreciated that when the FIG. 6 arrangement is used in the assembly of FIGS. 1 and 2, it permits automatic loading and unloading of the tube 9, thereby overcoming a major problem with prior peristaltic pumps. In particular, the tube 9 is not left in a stressed condition as sometimes happens with prior pumps, and therefore has an extended useful life, although in a preferred construction of the present invention, the tube 9 is only minimally tensioned, as described above.

The operative surface 10 of the presser plate 10 may be profiled in a manner such as to either eliminate pulsations in the output flow, or minimise the adverse consequences of any such pulsations. That profiling may be such that the surface 10 has two distinct regions, a pinch region 25 and an expansion region 26, both of which are shown in FIG. 7. In the preferred arrangement shown in FIG. 7 however, there is a third region 27 which will be referred to as the entrance region. The expansion region 26 is located downstream of the pinch region 25 relative to the direction of flow through the tube 9, and the entrance region 27 is located upstream of the pinch region 25.

In the particular arrangement shown in FIG. 7, the pinch region 25 extends through an arc of approximately 24°, the extremities of which are defined by lines 28 and 29 which extend radially from a point 30. It is preferred that the surface region 25 is of uniform radius, the center of which is located at the point 30. Furthermore, in the installed condition of the presser plate 7, the point 30 is preferably substantially coincident with the axis 4 about which the drum 2 rotates. The arcuate length of the pinch region 25 may be determined by the number of rollers 5 (that is, 24° is appropriate for a pump having 15 rollers 5) but may vary according to requirements, and consequently the 24° extent of the arrangement shown should not be understood as critical or essential.

A feature that may be incorporated in the pump is to arrange for the tube 9 to be "oversquashed" in a portion or all of the pinch region, that is, to arrange for the tube walls to be squeezed together slightly beyond the limit necessary to effect a seal. This feature admits of greater manufacturing and assembly tolerances for the pump parts.

The expansion region 26 also follows a curved path, but is arranged so that the distance between that path and the periphery of the drum 2 progressively increases in the downstream direction. As previously indicated, the profile of the surface region 26 is preferably designed to achieve a substantially linear relationship between the angular rotation of the drum 2 and the increasing internal volume of the tube 9 which follows withdrawal of the rollers 5 from contact with the tube 9. One possible approach is to construct a linear expansion profile of the surface region 26 from the equation $R=RO+KA$, where:

R is the radius of curvature of the surface region 26 at a particular point in that region, RO is the radius of curvature of the pinch region 25, K is a constant defining the rate of expansion of the tube 9, and A is the angle of rotation of the drum 2 beyond the point at which the surface region 26 commences.

The extent to which pulsations are reduced depends upon the value selected for K. A flow pulsation of approximately 10% is achievable using an optimal value for K for the roller system that is employed.

If a parabolic expansion curvature is selected for the region 26, flow pulsations in the region of 8.5% may be achieved, whereas an exponential profile can achieve a better result with residual pulsations in the order of 5.7%. A satisfactory profile, and the equation for generating that profile, can be determined according to individual needs.

In the particular arrangement shown in FIG. 7, the extremities of the expansion region 26 are defined by the lines 28 and 31 which extend radially from the point 30. The angular extent of the surface region 26 is approximately 66° in the arrangement shown, but a different angular extent may be selected.

The surface region 27 is preferably arranged to achieve progressive compression of the tube 9 as the drum 2 advances over the tube section 13. Any suitable curvature can be selected for that purpose, Subject only to the requirement that the separation between the surface region 27 and the drum periphery decreases in the downstream direction. The angular extent of the region 27 is defined by the radial lines 29 and 32, and in the example shown it is approximately 66°, that is, equal to the expansion region.

It is preferred to provide a membrane 33 (FIG. 1) between the drum 2 and that part of the tube 9 which is subjected to the influence of the presser plate 7. The upstream end 34 of the membrane 32 may be anchored in any appropriate fashion so as to be fixed against movement with the drum 2, and the anchoring point 35 need not be located as shown in FIG. 1. The downstream end 36 of the membrane 33 may be anchored also, but preferably in such a way as to allow some movement of that end in the longitudinal direction of the tube 9.

The purpose of the membrane 33 is to absorb shear forces generated by frictional resistance to rotation of the rollers 5 and thereby protect the tube 9 against longitudinal stretching. It is desirable that the membrane 33 be sufficiently flexible not to hinder expansion of the tube 9 into the region between adjacent rollers 5 as shown in FIG. 3. It is also desirable that the membrane 33 be resistant to stretching in the longitudinal direction of the tube 9 when subjected to the forces generated by the presser plate 7 in the pump operative position. Suitable materials for the membrane 33 include plastics films such as polyester. Mylar having a thickness in the range of 0.1 millimeter to 0.2 millimeter has been found to be satisfactory.

When the presser plate 7 is in the operative position, the membrane 33 is sandwiched between the rollers 5 and the operative surface 10 of the plate 7. Thus, the membrane 33 supplies the forces required to overcome frictional resistance to rotation of the rollers 5, and thereby absorbs the associated shear forces. Since the membrane 33 does not stretch, all shear and tension forces are eliminated from the tube 9, which is held in its operative position between supports 14 and 15 such that virtually a zero tension force is applied to it between those supports. That not only eliminates flow pulsations induced by longitudinal stretching of the tube 9, but also leads to longer tube life and more stable flow characteristics because of the elimination of shear force fatigue failures.

The example pump 1' shown in FIG. 8 is similar to the pump described in FIGS. 1–7 (note that the same reference numerals, but with a prime, have been used in FIG. 8 to denote features that correspond in the two embodiments) except that instead of having a rotatable drum and rollers, it includes a drum in the form of a cam 3', arranged for rotation about an axis 4'. Cam 3' has a plurality of camming surfaces 5' extending as a continuous series around its periphery. The number of camming surfaces 5' on cam 3' may be chosen to optimise flow linearity, for example, the number of surfaces 5' depicted in the FIG. 8 embodiment, namely 15, may be increased to reduce the magnitude of each flow pulsation, although the frequency of the pulses will be increased. Each surface 5' is circular in profile, although it is within the scope of the invention to employ other than a circular profile for the camming surfaces.

A membrane 33' is provided between the cam 3' and that part of the tube 9' which is subjected to the influence of the presser plate 7'. As in the FIGS. 1–7 embodiment, the purpose of the membrane 33' is to absorb shear forces generated by frictional resistance to rotation of the Cam 3' and thereby protect the tube 9' against longitudinal stretching.

Suitable materials for the membrane 33' include plastics films such as polyester, particularly materials which are highly slippery so as to reduce frictional forces between the camming surfaces 5' and the membrane. An example of a particularly suitable material is Ultra High Molecular Weight Poly Ethylene (UHMWPE). Membrane 33' may be a laminate of Mylar and UMMWPE, and be positioned such that the ITHMWPE faces the camming surfaces 5' in order to minimise the frictional force between the membrane and surfaces 5' as they slide along the membrane. Preferably the membrane is such as to consist entirely of the one material.

It should be noted that as the tube 9 ages, if some extension of it does occur due to the cumulative effects of squashing pressure being applied by the presser plate and compressing elements, the tube supports 14 and 15 as shown in the figures are such as will allow for any such increase in tube length while still correctly holding the tube in its operating position.

According to a preferred feature of the invention a cyclically varying holding force is applied to the presser plate 7 or 7' by an electro-mechanical actuator. This may be done by varying the electrical power supplied to the actuator from a control system (not shown), cyclically at a convenient frequency such that the maximum Current variation from a mean is that current which approaches that required to overcome the internal friction of the actuator. This is known as "dithering".

A peristaltic pump as described is ideally suited for use in spectroscopic apparatus for delivering a sample to the nebulizer of such apparatus. An example arrangement of that kind is shown diagrammatically by FIG. 9.

Figure 9:
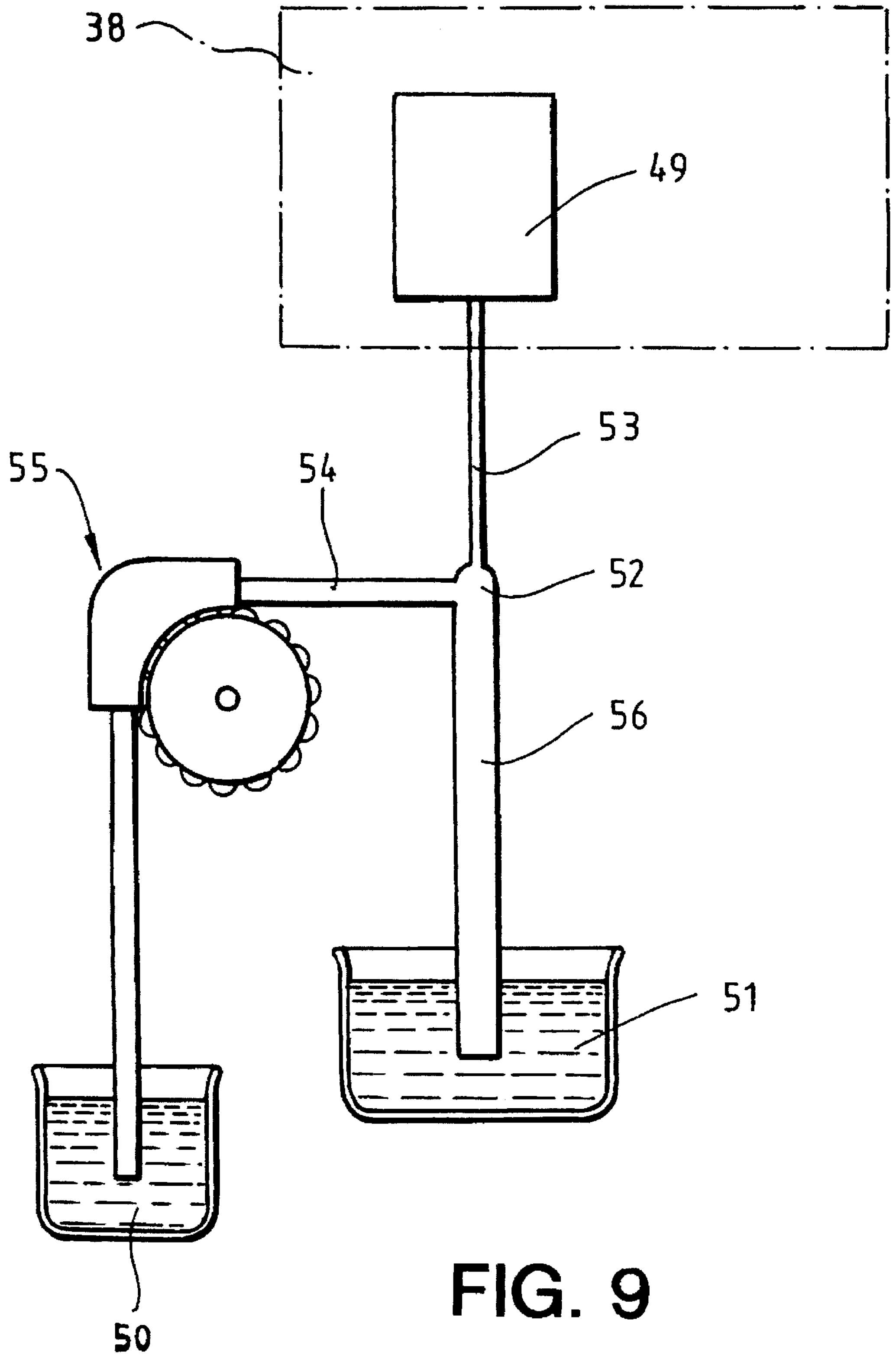
FIG. 9 is a diagram of a system for delivering a sample to spectroscopic apparatus, and which represents an example use of a pump according to the present invention.

In the FIG. 9 arrangement, a nebulizer 49 is shown which forms part of spectroscopic apparatus 38. Nebulizer 49, a sample solution supply 50 and a diluent supply 51, are each separately connected to a junction 52. The connection between the junction 52 and the nebulizer 49 is by way of a feed passage 53 which is preferably of relatively small cross-sectional size for a reason hereinafter made clear. The sample solution supply 50 is connected to the junction 52 through a delivery passage 54 and a peristaltic pump 55 (as previously described in relation to FIGS. 1–7 or FIG. 8) having its output side connected to that passage. The diluent supply 51 is connected to the junction 52 through a passage 56 which preferably has a relatively large cross-sectional size by comparison with that of the feed passage 53.

It is a feature of the arrangement shown that the pump 55 is controllable to deliver sample solution through the passage 54 at any of a variety of precisely controllable flow rates.

Because of the relatively small size of the feed passage 53, it exhibits a high resistance to flow. The passage 56 on the other hand, exhibits relatively low resistance to flow. As a consequence of that difference, substantially all the pressure drop in the system illustrated occurs between the nebulizer 49 and the junction 52. A nebulizer of the kind used in spectrophotometers will usually generate a stable pressure reduction at the liquid intake port, and in that event the flow rate through the passage 53 will be substantially constant and stable.

If the pump 55 is operated to deliver sample solution to the junction 52 at a flow rate slightly below the natural aspiration rate through the feed passage 56, the solution will enter the nebulizer 49 in almost undiluted form. Assuming that the solution is found to have a concentration above the desirable range, the speed of the pump 55 can be reduced to thereby reduce the flow rate through the delivery passage 54 and consequently cause increased diluent to be induced into the stream flowing through the feed passage 56. Thus, the pump speed can he adjusted to obtain a satisfactory dilution ratio in the stream entering the nebulizer 49.

The sample concentration in the atomized body which is measured by the spectrometer, is thereby directly proportional to the rate of flow through the delivery passage 54, which is in turn proportional to the speed of operation of the pump 55. It is therefore possible to accurately and quickly adjust the dilution ratio as required.

If operation of the pump 55 is stopped for any reason, such as to change the sample solution, the nebulizer 49 will continue to aspirate diluent from the supply 50. As a result, the nebulizer and associated spray chamber do not dry out as occurs in conventional systems, but are subjected to rinsing by the clean diluent. That maintains the nebulizer and spray chamber in ideal condition for the next sample measuring operation.

Since the diluent will usually have zero absorbance, a system as described above can carry out an auto zero function during the time that diluent alone is passing through the nebulizer. That has the advantage of improving the system performance and simplifying user interaction.

The system described can also be used for micro sampling. The pump 55 can be briefly operated to inject a small quantity of sample solution into the diluent stream passing through the feed passage 53. There is no change in the flow through the nebulizer during that micro sampling operation, and consequently the nebulizer characteristics remain stable. That is in contrast with conventional micro sampling involving brief introduction of the sampling tube into the sampling liquid while the nebulizer aspirates air immediately before and immediately after that introduction of the sampling tube.

The use of a peristaltic pump, because of its flow through characteristics, means there are no separate fill or flush stages as would be necessary with a syringe pump and which slow down the operating sequence. Furthermore, a multi channel peristaltic pump could be used so as to simultaneously pump several liquids each of which has a fixed flow rate determined by the cross-sectional size of the respective channel (tube) through which it flows. By way of example, use of three tubes or channels for sample, acidifier and sodium borohydride respectively, makes it possible to use the system described for hydride operations.

Figure 10:
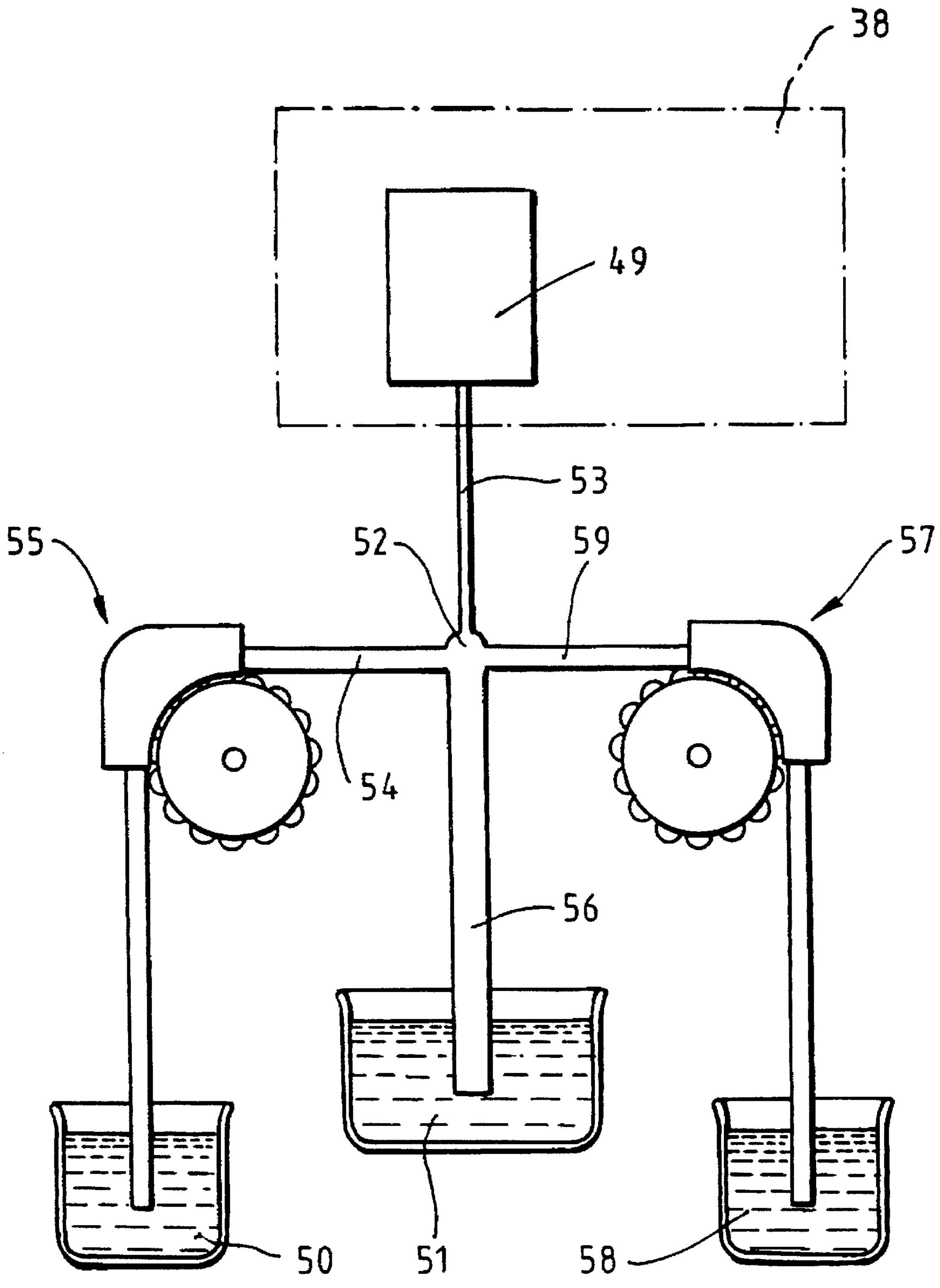
FIG. 10 is a diagrammatic representation of a modified system to that shown in FIG. 9, which allows standard additions to be carried out.

FIG. 10 shows a modified form of the system described in relation to FIG. 9 in which there is added a second pump 57 connected to a supply 58 of standard solution and also connected to the junction 52 through a delivery passage 59 to a third part of the junction 52. The pump 57 is a variable speed peristaltic pump as described in relation to FIGS. 1–7 or FIG. 8 so that control of the relative speeds of the two pumps 55 and 57 enables an accurate ratio of sample to standard to be maintained.

The modified system is intended for use in relation to the well known standard additions technique, which involves measuring the sample and then measuring the sample spiked with an additional known amount of analyte. It is possible to determine the concentration of analyte in the original (non-spiked) sample by comparing the two measurements.

Standard additions as carried out in conventional systems has a number of deficiencies. By way of example, a linear regression line is usually drawn through the spiked and unspiked absorbance readings. That assumes the existence of a linear calibration curve, and yet it is known that AA calibration curves are not linear at high concentrations of analyte. Although several samples spiked to different degrees could he analysed and used to compute a non linear calibration curve, the amount of operator time and effort necessary to prepare and measure the samples would be significant and is therefore seldom done.

Furthermore, spiking the sample changes the ratio of matrix to analyte concentration and therefore changes the effect of the matrix. In order to minimise that result, it is desirable that the spike only increase the total analyte concentration by a reasonable amount. At the same time, a small spike may yield poor precision in the measurement results because of the small difference between the spiked and unspiked readings. In conventional standard additions analysis however, both the unspiked and spiked samples need to be available at the time of the analysis and therefore the spiked sample must be prepared without knowing even the approximate concentration of the analyte in the sample. This means that the change in concentration introduced by the spiking could be very large (e.g., 10 or even 100 times for low concentration samples), or conversely very small for high concentration samples. In order to overcome that problem, it is necessary to first analyse the sample by conventional calibration to obtain an approximate analyte concentration, and use that information to determine the amount of spiking. Such an approach necessarily doubles the operator work load.

In addition to the foregoing, standard additions using conventional AA instrumentation is extremely slow, operator intensive and prone to error. Whereas in the case of normal calibration the operator only prepares the sample and can analyse the sample in a few seconds, for standard additions the operator must prepare and analyse at least one additional solution (and often more than one) involving accurate weighing, measuring and mixing. The time per sample is increased from a few seconds to several minutes.

A system of the general kind diagrammatically illustrated in FIG. 10 has the benefit of overcoming or at least minimising the aforementioned problems. That is particularly the case by use of a method as described below.

A preferred method using the system of FIG. 10 involves the following steps:

(a) measure the sample, (b) if the measured absorbance is above 50% of the linear range, dilute the sample, (c) measure the diluted sample, (d) add a standard to the sample so as to approximately double the absorbance, (e) measure the spiked sample, and (f) compare measurement (e) with measurement (a) or (c) as appropriate.

In the event that dilution of the sample is not required, the measurement comparison will of course be between the measurement referred to under (a) above and the measurement referred to under (e). In the case of a diluted sample the comparison will be between the. measurement referred to in (c) above and the measurement referred to in (e).

The method described above has the benefit that the operator is only required to present a single sample as normal calibration, and because all dilutions and additions are carried out in line it is possible to achieve a high throughput, It will be apparent from the foregoing description that the system according to the present invention provides improvements in both normal calibration and standard additions. Operator time is minimised without sacrifice of accuracy in the results of the analysis.

It will be also evident from the foregoing that a pump according to the present invention overcomes substantial problems existing in prior peristaltic pumps, and in particular provides a peristaltic pump which is suitable for use in situations requiring a stable and accurate flow rate. Furthermore, a peristaltic pump as shown in FIG. 8 is of more simple construction, having fewer moving parts (thus providing a mechanism that is less prone to corrosion) and in which the need for very small manufacturing and assembling tolerances is reduced.

Finally, it is to be understood that various alterations, modifications and/or additions may be introduced into the constructions and arrangements of parts previously described without departing from the spirit or ambit of the invention as defined in the appended claims.

We claim:

1. A system for delivering a sample for analysis to spectroscopic apparatus, comprising a peristaltic pump for supplying a stream of sample solution at a selectable flow rate to a first inlet port of a fluid stream combiner, said combiner having a second inlet port communicating through a feed passage of relatively large cross-sectional area with a source of diluent, the outlet of said fluid combiner communicating through a feed passage of relatively small cross sectional area with a nebulizer of said spectroscopic apparatus wherein substantially all of the pressure drop in the system occurs across the feed passage of relatively small cross sectional area and a substantially constant flow rate therethrough is determined by the natural aspiration of said nebulizer, and whereby upon variation of said flow rate of sample, the stream of said diluent varies to maintain said constant flow rate through said outlet feed passage to said nebulizer.

2. A system as claimed in claim 1 further including means for supplying a stream of standard solution to a third port connected to said fluid stream combiner which means for supplying a stream of standard solution also includes a peristaltic pump.

3. A system as claimed in claim 2, wherein-the standard solution supply means includes a feed passage connected between the outlet of the second mentioned peristaltic pump and the said fluid stream combiner.

4. A method of spectroscopic analysis, wherein a system as claimed in claim 3 is used to supply a sample to a nebulizer of spectroscopic apparatus for calibration of that apparatus and for analysis of the sample, the method including supplying streams of sample solution from a single on-line source of the sample solution.

5. A method as defined in claim 4, wherein a standard additions technique of analysis is employed, the method including diluting the stream of the sample solution and spiking it with the standard solution from a single on-line source of diluent and a single on-line source of standard solution.

* * * * *